(12) United States Patent
Shiota et al.

(10) Patent No.: US 9,968,624 B2
(45) Date of Patent: May 15, 2018

(54) DEPRESSION TREATMENT AGENT

(71) Applicant: THE UNIVERSITY OF TOKYO, Tokyo (JP)

(72) Inventors: Kunio Shiota, Tokyo (JP); Shintaro Yagi, Tokyo (JP); Koji Hayakawa, Tokyo (JP); Mitsuko Takamori, Tokyo (JP); Takefumi Kikusui, Sagamihara (JP); Yukishige Ito, Wako (JP); Yasuharu Sakamoto, Wako (JP); Hideharu Seto, Wako (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days. days.

(21) Appl. No.: 15/311,511

(22) PCT Filed: May 15, 2015

(86) PCT No.: PCT/JP2015/064105
§ 371 (c)(1),
(2) Date: Nov. 15, 2016

(87) PCT Pub. No.: WO2015/174532
PCT Pub. Date: Nov. 19, 2015

(65) Prior Publication Data
US 2017/0080004 A1    Mar. 23, 2017

(30) Foreign Application Priority Data
May 16, 2014 (JP) ................................ 2014-102104

(51) Int. Cl.
*A61K 31/7008*    (2006.01)
(52) U.S. Cl.
CPC ................................ *A61K 31/7008* (2013.01)
(58) Field of Classification Search
CPC ................................................ A61K 31/7008
USPC ........................................................ 514/23
See application file for complete search history.

(56) References Cited

U.S. PATENT DOCUMENTS

| 6,274,568 B1 * | 8/2001 | Schnaar ................. C07H 13/04 435/7.1 |
| 8,987,232 B2 * | 3/2015 | Shiota ................. A61K 31/7008 514/62 |
| 9,271,995 B2 * | 3/2016 | Shiota ................. A61K 31/7008 |
| 2009/0012043 A1 | 1/2009 | Moe et al. |
| 2009/0214439 A1 | 8/2009 | Kumar et al. |
| 2011/0212917 A1 * | 9/2011 | Shiota ................. A61K 31/7008 514/62 |
| 2014/0349964 A1 | 11/2014 | Shiota et al. |
| 2015/0259371 A1 | 9/2015 | Vocadlo et al. |

FOREIGN PATENT DOCUMENTS

| JP | H10-182685 A | 7/1998 |
| JP | 2001-078794 A | 3/2001 |
| JP | 2009-530311 A | 8/2009 |
| JP | 2009-292763 A | 12/2009 |
| JP | 2010-532388 A | 10/2010 |
| JP | 2011-179702 A | 9/2011 |
| WO | WO 2010/027028 A1 | 3/2010 |
| WO | WO 2011/137528 A1 | 11/2011 |
| WO | WO 2013/047773 A1 | 4/2013 |
| WO | WO 2013/068935 A1 | 5/2013 |

OTHER PUBLICATIONS

Patani et al, Chem. Rev., 1996, 96, 3147-3176.*
Gelenberg et al., Practice Guideline for the Treatment of Patients with Major Depressive Disorder, Third Edition, American Psychiatric Association (Oct. 2010).
Hasegawa et al., "Synthesis of 2-acetamido-2-deoxy-5-thio-α-D-mannopyranose," *Carbohydrate Research*, 122: 168-173 (1983).
Takeda et al., "General Proposal of Depression Methods," *Japanese Journal of Biological Psychiatry*, 21(3): 155-182 (2010).
Japanese Patent Office, International Search Report in International Patent Application No. PCT/JP2015/064105 (dated Jun. 30, 2015).

* cited by examiner

*Primary Examiner* — Ganapathy Kirshnan
(74) *Attorney, Agent, or Firm* — Leydig, Voit & Mayer, Ltd.

(57) ABSTRACT

The invention provides an agent for treating depression, which contains N-acetyl-D-mannosamine, and a pharmaceutical composition for treating depression, which contains an effective amount of N-acetyl-D-mannosamine and a carrier acceptable as a medicament.

6 Claims, 4 Drawing Sheets

DEPRESSION TREATMENT AGENT

CROSS-REFERENCE TO RELATED APPLICATIONS

This patent application is the U.S. national phase of International Patent Application No. PCT/JP2015/064105, filed May 15, 2015, which claims the benefit of Japanese Patent Application No. 2014-102104, filed on May 16, 2014, which are incorporated by reference in their entireties herein.

TECHNICAL FIELD

The present invention relates to an agent for treating depression, and relates to a therapeutic drug containing N-acetyl-D-mannosamine as an active ingredient.

BACKGROUND ART

Depression is a maximum cause of life's disability due to a disease, and is a disease considered to be important as a factor of suicide (non-patent documents 1 and 2). Antidepressants are largely divided into tricyclics, tetracyclics, triazolopyridines, SSRI (Selective Serotonin Reuptake Inhibitor), and SNRI (Serotonin Noradrenalin Reuptake Inhibitor). These antidepressants have a reuptake inhibitory action on noradrenaline or serotonin or a certain level of dopamine. However, a treatment effect by these drugs is limitative.

N-acetyl-D-mannosamine, which is an isomer of N-acetyl-D-glucosamine, is known as, for example, a starting material for enzymatic synthesis of sialic acid (N-acetylneuraminic acid) to be a pharmaceutical product and a starting material of a medicament. Since a sialic acid derivative can be enzymatically synthesized from a derivative of N-acetyl-D-mannosamine, N-acetyl-D-mannosamine is an industrially important substance. As a production method of N-acetyl-D-mannosamine, a method including addition of boric acid or borate during isomerization of N-acetylglucosamine under alkaline conditions, thereby increasing a mole conversion yield into N-acetylmannosamine, is known (patent document 1). In addition, a method of producing N-acetyl-D-mannosamine by reacting N-acetylneuraminate lyase with sialic acid as a substrate is also known (patent document 2). A method of controlling lectin binding to cell surface and a method of regulating nerve cell growth, by contacting acylated body of N-mannosamine with cells have been proposed (patent document 3). In patent document 3, N-acetyl-D-mannosamine is regarded as a negative control in promoting growth of axon in vitro.

The present inventors have found that N-acetyl-D-mannosamine is effective for improving brain hypofunction or improving sleep disorder (patent documents 4 and 5).

DOCUMENT LIST

Patent Documents patent document 1: JP-A-10-182685
patent document 2: JP-A-2001-78794
patent document 3: U.S. Pat. No. 6,274,568
patent document 4: WO 2010/027028
patent document 5: JP-A-2011-178702

Non-Patent Documents non-patent document 1: Japanese Journal of Biological Psychiatry 21(3): 155-182, 2010 non-patent document 2: Practice Guideline for the Treatment of Patients with Major Depressive Disorder Third Edition American Psychiatric Association, 2010

SUMMARY OF THE INVENTION

Problems to be Solved by the Invention

Many people experience mental disorders including depression. As mentioned above, depression is a maximum cause of life's disability due to a disease, and is an important factor of suicide, as well as changes endocrine system and immune system, and adversely influences progression of physical diseases. For example, depression increases onset of diabetes and mortality from diabetes, promotes arteriosclerosis, increases the risk of myocardial infarction and cerebral infarction, and increases mortality from cancer. However, as the situation stands, many depression patients are not treated sufficiently. An object of the present invention is to provide an antidepressant useful for depression.

Means of Solving the Problems

The present inventors have conducted intensive studies and unexpectedly found that administration of N-acetyl-D-mannosamine to a depression animal model remarkably improves the symptom, which resulted in the completion of the present invention. Therefore, the present invention provides the following.

[1] A therapeutic agent for depression, comprising N-acetyl-D-mannosamine.
[2] The therapeutic agent of [1], wherein the N-acetyl-D-mannosamine is a compound selected from the group consisting of the compounds represented by the following formulas (I), (IIa), (IVa), (IVb) and (IVc):

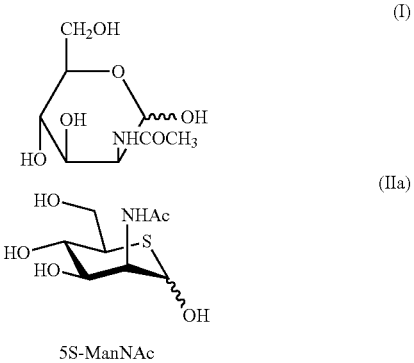

wherein Ac is an acetyl group

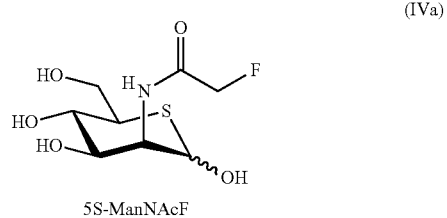

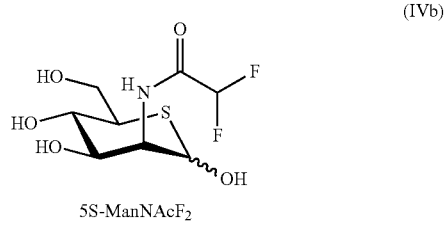

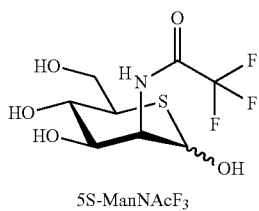

5S-ManNAcF₃ or a salt thereof.

[3] The therapeutic agent of [1], wherein the N-acetyl-D-mannosamine is a compound represented by the following formula (IVa):

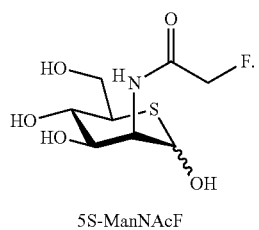

5S-ManNAcF

[4] The therapeutic agent of any of [1]-[3], which is an oral preparation, injection, drip infusion or external preparation.

[5] A pharmaceutical composition for treating depression, which comprises an effective amount of N-acetyl-D-mannosamine and a carrier acceptable as a medicament.

[6] The pharmaceutical composition of [5], wherein the N-acetyl-D-mannosamine is a compound selected from the group consisting of the compounds, represented by the following formulas (I), (IIa), (IVa), (IVb) and (IVc):

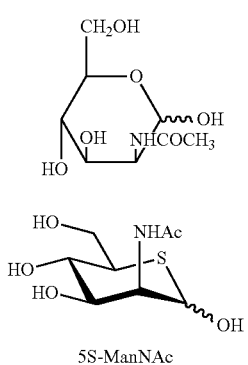

5S-ManNAc wherein Ac is an acetyl group

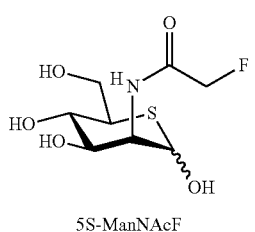

5S-ManNAcF

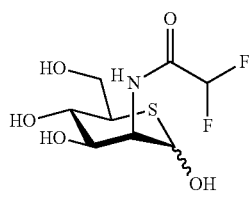

5S-ManNAcF₂

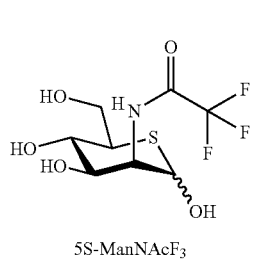

5S-ManNAcF₃ or a salt thereof.

[7] The pharmaceutical composition of [5], wherein the N-acetyl-D-mannosamine is a compound represented by the following formula (IVa):

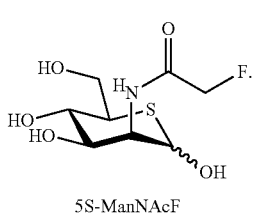

5S-ManNAcF

[8] The pharmaceutical composition of any of [5]-[7], which is a dosage form for intravenous, intramuscular, intracerebrospinal fluid or oral administration.

[9] Use of N-acetyl-D-mannosamine in the production of a medicament for treating depression.

[10] The use of [9], wherein the N-acetyl-D-mannosamine is a compound selected from the group consisting of the compounds represented by the following formulas (I), (IIa), (IVa), (IVb) and (IVc):

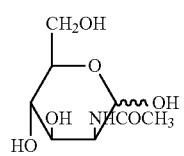

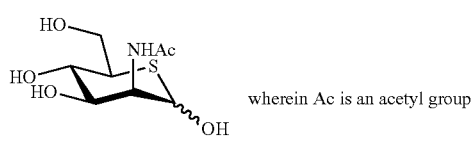

wherein Ac is an acetyl group

5S-ManNAc

-continued

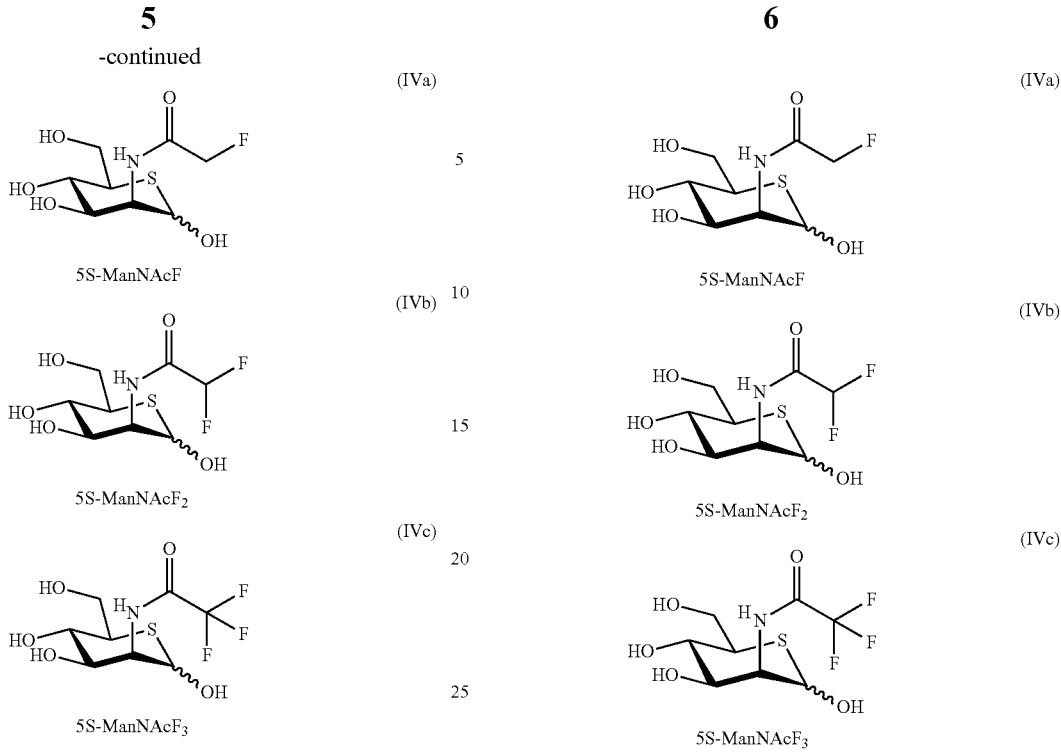

or a salt thereof.

[11] The use of [9], wherein the N-acetyl-D-mannosamine is a compound represented by the following formula (IVa):

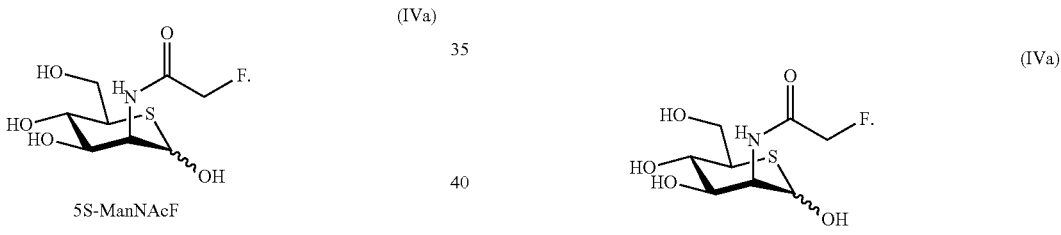

[12] A method of treating depression, comprising a step of administering an effective amount of N-acetyl-D-mannosamine to a subject in need thereof.

[13] The treatment method of [12], wherein the N-acetyl-D-mannosamine is a compound selected from the group consisting of the compounds represented by the following formulas (I), (IIa), (IVa), (IVb) and (IVc):

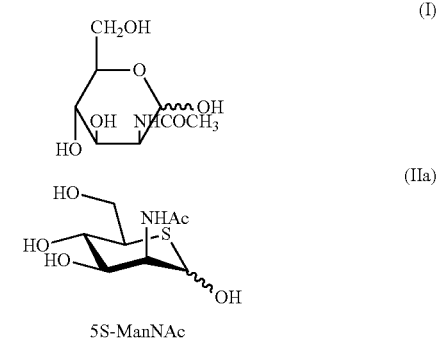

wherein Ac is an acetyl group or a salt thereof.

[14] The treatment method of [12], wherein the N-acetyl-D-mannosamine is a compound represented by the following formula (IVa):

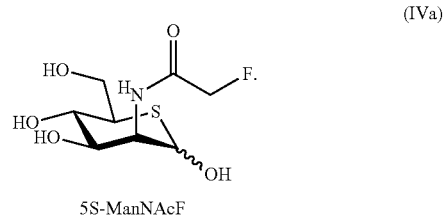

Effect of the Invention

N-acetyl-D-mannosamine is effective for the psychological symptoms and physical symptoms that the patients affected with depression show. The therapeutic agent of the present invention containing N-acetyl-D-mannosamine as an active ingredient can be used in combination with existing antidepressants, and can be administered to patients in parallel with mental therapy or physical therapy of depression. Furthermore, the therapeutic agent of the present invention is also useful for preventing recurrence of depression.

DESCRIPTION OF EMBODIMENTS

Figure 1:
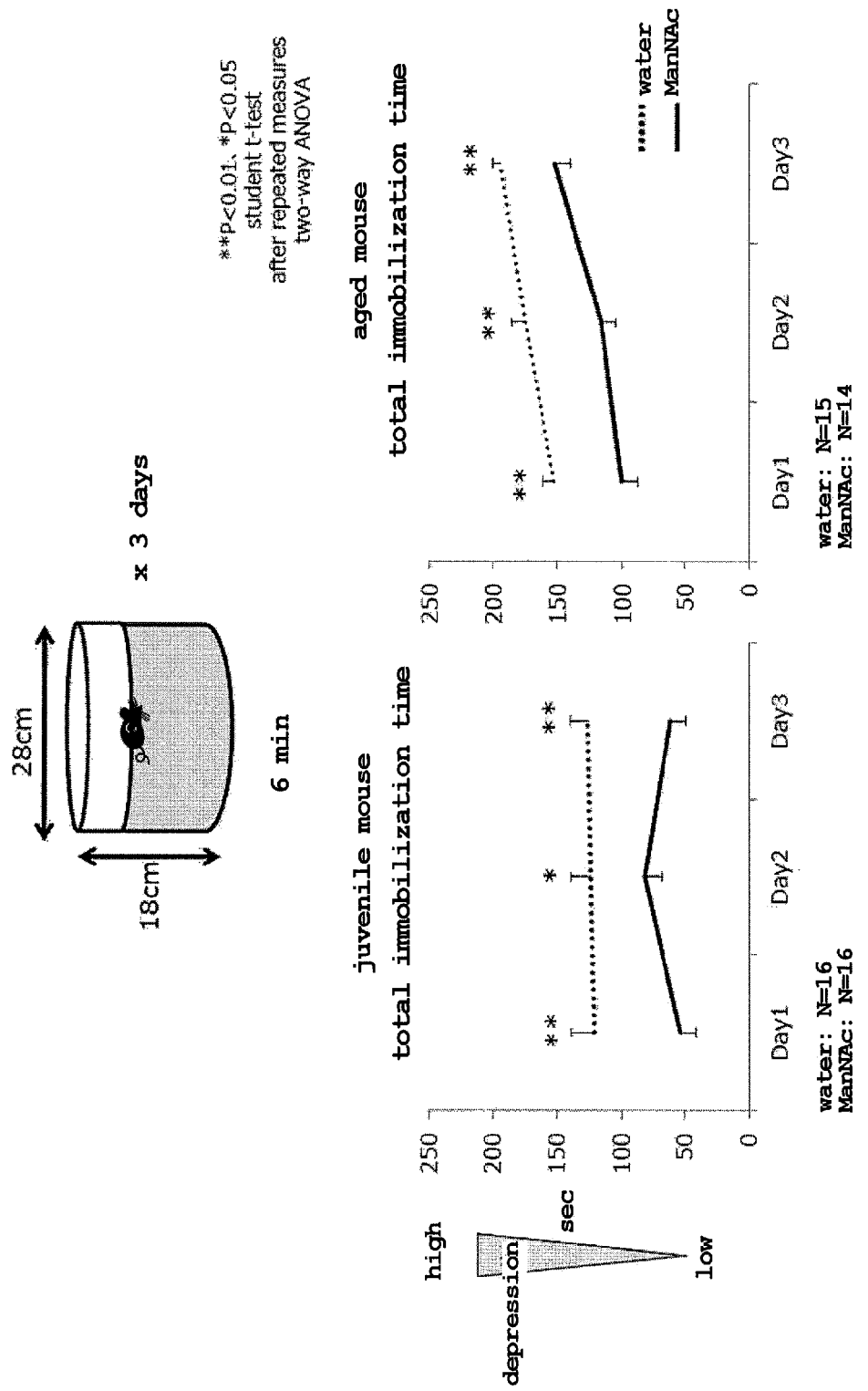
FIG. 1 shows an outline of the forced swim test of Example 1 and the results thereof.

In the present invention, "depression" is as defined in DSM-5 (Diagnostic and Statistical Manual of Mental Disorders, 5th Edition), and encompasses clinical depression and depressive disorders.

The diagnosis of "depression" is defined in DSM-5. Alternatively, the diagnostic standard of depression is defined in ICD (International Statistical Classification of Diseases and Related Health Problems)-10, wherein the standard holds that the basic symptom includes at least two of the following.
1) lowering of mood
2) loss of emotion and pleasurable feelings
3) increase of fatiguability due to reduction of energy, decrease in activity In the present invention, N-acetyl-D-mannosamine may be an N-acetyl form of D-mannosamine, which is represented by the following formula (I):

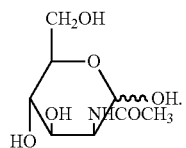

(I)

A compound represented by the formula (I) is sometimes to be abbreviated as "ManNAc".

In the present invention, N-acetyl-D-mannosamine is not limited to a single compound represented by the above-mentioned formula (I), but is a concept including a derivative thereof, a precursor or a prodrug, a salt thereof, and a solvate thereof (hereinafter sometimes to be abbreviated as "derivative and the like").

N-acetyl-D-mannosamine may be, for example, a compound represented by the following formula (II).

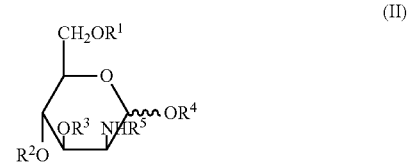

(II)

wherein $R^1$, $R^2$, $R^3$ and $R^4$ are each independently hydrogen (H), $R^6$, —C(=O) $R^6$, —C(=O)$OR^6$ or —C(=O) $NR^6R^7$, $R^6$ is a $C_{1-7}$ chain or cyclic hydrocarbon optionally having substituent(s), $R^7$ is hydrogen (H), a $C_{1-7}$ chain or cyclic hydrocarbon optionally having substituent(s), and $R^5$ is hydrogen (H), $R^6$, —C(=O)$OR^6$, —C(=O)$NR^6R^7$ or —C(=O)—$CH_2$—$R^8$, $R^6$ is a $C_{1-7}$ chain or cyclic hydrocarbon optionally having substituent(s), $R^7$ is hydrogen (H), a $C_{1-7}$ chain or cyclic hydrocarbon optionally having substituent(s), $R_8$ is a $C_{1-7}$ chain or cyclic hydrocarbon optionally having substituent(s), —$(CH_2)_n$—C(=O)$R^9$ (n is an integer of 1-6, and $R^9$ is $C_{1-6}$ alkyl), —NH—C(=O)$R^{10}$ ($R^{10}$ is a $C_{1-7}$ chain hydrocarbon optionally having substituent(s)), azido, oxycarbonyl-$C_{1-6}$ alkyl or thiocarbonyl-$C_{1-6}$ alkyl.

As the substituent, a halogen atom (fluorine, chlorine, bromine, iodine) can be used.

N-acetyl-D-mannosamine may be, for example, a compound represented by the following formula (IIa)-(IIc), (IIIa)-(IIIc) and (IVa)-(IVc), wherein Ac is an acetyl group.

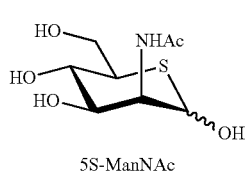

5S-ManNAc (IIa)

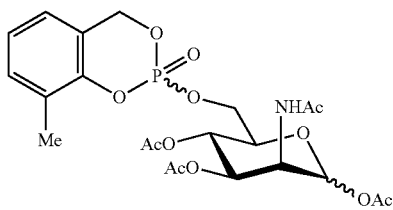

Ac₃ManNAc-6csP (IIb)

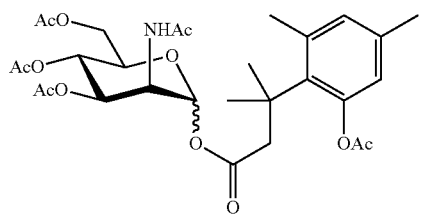

TML-Ac₃ManNAc (IIc)

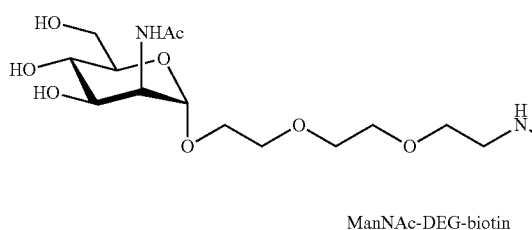 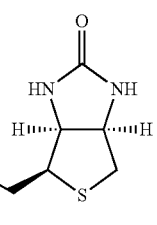

ManNAc-DEG-biotin (IIIa)

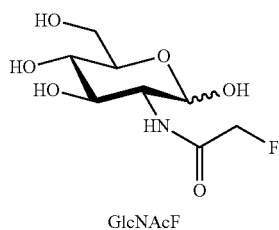

GlcNAcF

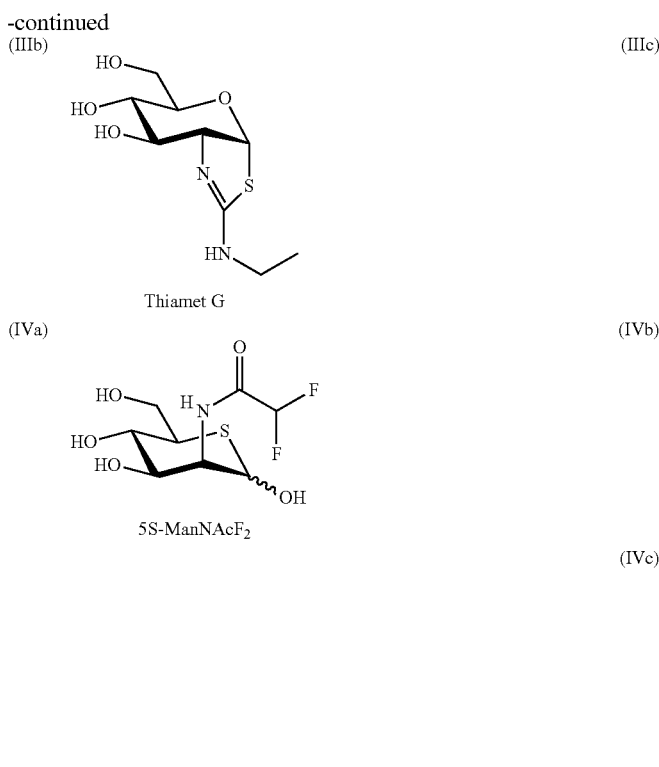

The derivative and the like of N-acetyl-D-mannosamine are also described in documents (Metabolic glycoengineering: Sialic acid and beyond Glycobiology 2009 vol. 19 (12) pp. 1382-1401 (particularly FIG. 4), Metabolic oligosaccharide engineering with N-Acyl functionalized ManNAc analogs: Cytotoxicity, metabolic flux, and glycan-display considerations Biotechnol Bioeng 2011 vol. 109 (4) pp. 992-1006 (particularly FIG. 2)), and also preferably used in the present invention.

Examples of the salt of N-acetyl-D-mannosamine include pharmacologically acceptable salts, for example, salt with inorganic acid, salt with organic acid, salt with basic or acidic amino acid and the like.

Examples of the salt with inorganic acid include salts with hydrochloric acid, hydrobromic acid, nitric acid, sulfuric acid, phosphoric acid and the like.

Examples of the salt with organic acid include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Examples of the salt with basic amino acid include salts with arginine, lysine, ornithine and the like, and examples of the salt with acidic amino acid include salts with aspartic acid, glutamic acid and the like.

Preferable examples of the solvate include hydrate (e.g., monohydrate, dihydrate and the like), ethanolate and the like.

N-acetyl-D-mannosamine is preferably ManNAc, 5S-ManNAc, 5S-ManNAcF$_2$, 5S-ManNAcF$_2$, 5S-ManNAcF$_3$ or a salt thereof, more preferably 5S-ManNAcF$_2$.

As N-acetyl-D-mannosamine, a commercially available product may be used, and one produced by a known method may also be used. Examples of the production method of N-acetyl-D-mannosamine represented by the formula (I) include, but are not limited to, a method including isomerizing N-acetylglucosamine under alkaline conditions (JP-A-10-182685), and a production method including reacting N-acetylneuraminate lyase with sialic acid as a substrate (JP-A-2001-78794). N-acetyl-D-mannosamine derivative and the like can also be produced by a method known per se, by using N-acetyl-D-mannosamine represented by the formula (I) as a starting material.

The compounds represented by the formulas (IIa) and (IVa)-(IVc) are generically referred to as 5S form in the present invention. Of the 5S form, a production method of 5S-ManNAc is put down in Hasegawa. E. Tanahashi, Y. Hioki, M. Kiso, Carbohydrate Res, 122, 168-173 (1983), 5S-ManNAc is hydrolyzed with hydrochloric acid, and treated with fluoromethyl acetate to give 5S-ManNAcF$_2$, 5S-ManNAcF$_2$ and 5S-ManNAcF$_3$ can also be synthesized by a similar method.

The "depression" which is the treatment target of the agent of the present invention is defined in DSM-5, and use of the International Classification of Disorder (ICD)-10 is recommended for the diagnosis thereof. Specifically, the detail is provided in "10 points of medical care for depression" produced by Japan Committee of Prevention and Treatment of Depression.

Whether or not the agent of the present invention is successfully effective for depression can be confirmed by utilizing a test consisting of plural question items used for diagnosis or analysis results of animal behavior pattern and the like, and from the test results after administration as compared to those before administration or improvement of behavior pattern.

As the agent of the present invention, N-acetyl-D-mannosamine can be used alone, or as a medicament or a food with health claims or food additive containing excipient (e.g., lactose, sucrose, starch, cyclodextrin etc.) and, in some cases, flavor, dye, seasoning, stabilizer, preservative and the like, and formulated as tablet, pill, granule, fine granule, powder, pellet, capsule, solution, skin milk, suspension, syrup, troch and the like. In addition, the agent of the present invention can also be used as a reagent for researches.

The amount of N-acetyl-D-mannosamine to be contained in the agent of the present invention is not particularly limited as long as it affords the effect of the present invention, and is generally 0.0001-100 wt %, preferably 0.001-99.9 wt %.

In addition, the present invention provides a pharmaceutical composition for the treatment of depression, which contains an effective amount of N-acetyl-D-mannosamine and a carrier acceptable as a medicament.

Examples of the carrier acceptable as a medicament include, but are not limited to, excipient (e.g., lactose, sucrose, dextrin, hydroxypropylcellulose, polyvinylpyrrolidone etc., disintegrant (e.g., starch, carboxymethylcellulose etc., lubricant (e.g., magnesium stearate etc., surfactant (e.g., sodium lauryl sulfate etc., solvent (e.g., water, brine, soybean oil etc., preservative (e.g., p-hydroxybenzoic acid ester etc.) and the like.

While the effective amount of N-acetyl-D-mannosamine is not particularly limited as long as an effect as a medicament can be afforded, it is generally 0.0001-99.5 wt %, preferably 0.001-99.0 wt %.

The agent or pharmaceutical composition of the present invention can be administered orally or parenterally to mammals (e.g., mouse, rat, rabbit, cat, dog, bovine, horse, monkey, human).

The present invention provides a food added with N-acetyl-D-mannosamine as an agent for treating depression.

The "food" in the present invention means foods in general, such as general foods including what is called health food, as well as food for specified health uses defined by the food with health claims system by the Ministry of Health, Labour and Welfare and food with health claims such as food with nutrient function claims and the like, and supplement, feed and the like are also encompassed in the food in the present invention.

For food use, N-acetyl-D-mannosamine can also be used by, for example, adding to general foods (including what is called health food) such as bread, confectionery and the like. In addition, N-acetyl-D-mannosamine together with excipient (e.g., lactose, sucrose, starch etc.) and, in some cases, flavor, dye and the like can be formulated into tablet, pill, granule, fine granule, powder, pellet, capsule, solution, skin milk, suspension, syrup, troch and the like, and used as food with health claims such as food for specified health uses, food with nutrient function claims and the like, or a supplement. The food of the present invention can also be applied to a feed use, and can be ingested by or administered to poultry, domestic animals and the like after addition to a general feed.

For ingestion as a food or feed, a standard ingestion frequency of the food or feed per day and a standard ingestion amount thereof per meal are roughly estimated, the amount of daily ingestion is defined, and the amount of N-acetyl-D-mannosamine to be contained in the daily ingestion amount of food or feed is determined. The content of N-acetyl-D-mannosamine can be determined based on the dose to be mentioned below.

The ingestion amount or dose of the agent, food or pharmaceutical composition of the present invention varies depending on the age, body weight and health conditions of the subject of ingestion or administration, and cannot be determined unconditionally. For example, 0.1-10 g, preferably 0.2 g-7 g, of N-acetyl-D-mannosamine can be ingested or administered per day in one to several portions. Depending on the kind of N-acetyl-D-mannosamine, it can be ingested or administered at a lower dose and, for example, in the case of 5S form and the like, 0.001-10 g, preferably 0.01 g-10 g, preferably 0.02 g-7 g, can be ingested or administered per day in one to several portions.

An administration method of the medicament (agent or pharmaceutical composition) of the present invention is not particularly limited as long as it is a pathway providing a prophylactic or therapeutic effect for depression. For example, it can be administered by parenteral administration (intravenous administration, intramuscular administration, intratissue direct administration, intranasal administration, intradermal administration, intracerebrospinal fluid administration and the like) or oral administration. Particularly, when the medicament is applied to human, it can be administered intravenously, intramuscularly or by oral administration. The dosage form is not particularly limited, and the medicament can be administered as various administration dosage forms, for example, oral preparation (granule, powder, tablet, sublingual tablet, film coating agent, sublingual film preparation, capsule, syrup, emulsion, suspension and the like), injection, drip infusion, external preparation (preparations for nasal administration, dermal preparation, ointment and the like).

The present invention also provides use of N-acetyl-D-mannosamine in the production of a medicament for treating depression. Specifically, the present invention provides a production method of a medicament for the prevention, improvement or treatment of depression, which uses N-acetyl-D-mannosamine.

As a production method of the medicament of the present invention, the methods known per se in the pharmaceutical field can be used without limitation.

The medicament of the present invention can be used in combination with one or more other drugs. In this case, the combination of the drugs is safer or more effective than the use of either drug alone. Such other drugs can be administered in the route and amount generally used for the drugs and simultaneously or continuously with the medicament of the present invention. When the medicament of the present invention is simultaneously used with one or more other drugs, a pharmaceutical composition in a unit dosage form containing such other drugs and N-acetyl-D-mannosamine is preferable. The combination therapy also includes a therapy comprising administering N-acetyl-D-mannosamine and one or more other drugs according to different overlapping schedules. When used in combination with one or more other active ingredients, use at a smaller dose of N-acetyl-D-mannosamine and the aforementioned other active ingredients than single use of each of them can also be assumed. Therefore, the pharmaceutical composition of the present invention includes one containing N-acetyl-D-mannosamine and one or more other active ingredients. The aforementioned combination includes not only N-acetyl-D-mannosamine and one other active compound, but also a combination with two or more other active compounds.

The weight ratio of N-acetyl-D-mannosamine to the second active ingredient may vary and is dependent on the effective dose of each component. In general, each effective dose is used. Therefore, for example, when. N-acetyl-D-mannosamine is combined with other drug, the weight ratio of N-acetyl-D-mannosamine to other drug is generally about 1000:1 to about 1:1000, preferably about 200:1 to about 1:200. A combination of N-acetyl-D-mannosamine and other active ingredient is also generally within the aforementioned range, or an effective dose of each active ingredient should be used for each case. In such combination, N-acetyl-D-mannosamine and other active drug can be administered individually or concurrently. Furthermore, administration of one factor may be before administration of other drug, simultaneously with the administration, or after the administration.

The medicament of the present invention can be used in combination with a drug currently used for the treatment of depression or a drug currently under development as an agent for the treatment of depression. The medicament of the present invention can be administered in combination with other compounds known in this field to be useful for the treatment of depression.

The medicament of the present invention can be used in combination with antidepressants including selective serotonin reuptake inhibitor (SSRI), dopamine and norepinephrine reuptake inhibitor, serotonin and norepinephrine reuptake inhibitor (SNRI), serotonin modulator, norepinephrine-serotonin modulator, tricyclic antidepressant, tetracyclic antidepressant, and monoamineoxydase inhibitor (MAOI).

Examples of SSRI include fluvoxamine, citalopram, escitalopram, fluoxetine, paroxetine, sertraline and salts thereof acceptable as medicaments and the like.

Examples of dopamine and norepinephrine reuptake inhibitor include bupropion and salts thereof acceptable as medicaments and the like.

Examples of SNRI include milnacipran, venlafaxine, desvenlafaxine, duloxetine and salts thereof acceptable as medicaments and the like.

Examples of serotonin modulator include nefazodone, trazodone and salts thereof acceptable as medicaments and the like.

Examples of norepinephrine-serotonin modulator include mirtazapine and salts thereof acceptable as medicaments and the like.

Examples of tricyclic antidepressant include amitriptyline, clomipramine, doxepin, imipramine, triimipramine, amoxapine, desipramine, maprotiline, nortriptyline, protriptyline and salts thereof acceptable as medicaments and the like.

Examples of tetracyclic antidepressant include mianserine, setiptiline and salts thereof acceptable as medicaments and the like.

Examples of triazolopyridine antidepressant include trazodone hydrochloride and the like.

Examples of MAOI include phenelzine, tranylcypromine, isocarboxazid, selegiline, moclobemide and salts thereof acceptable as medicaments and the like.

Alternatively, a combination with a supplement drug (antianxiety drug, antipsychotic agent, lithium salt and the like) is also possible.

A pharmaceutical composition for the administration of N-acetyl-D-mannosamine can be conveniently given in a unit dosage form, and can be prepared by any method well known in the field of pharmaceuticals. All methods include a step for combining carrier(s) constituting one or more aid components and an active ingredient. In general, a pharmaceutical composition is prepared by uniformly and completely mixing a liquid carrier or a finely-divided solid carrier or both of them with an active ingredient, and molding, as necessary, the product into a desirable dosage form. A pharmaceutical composition contains the object active compound in an amount sufficient to afford a desirable effect on the process or state of a disease. The term "composition" to be used in the present specification encompasses a product containing a designated amount of a designated component and any product obtained directly or indirectly from a combination of a designated amount of a designated component.

A pharmaceutical composition for oral use can be prepared according to any method known in the field relating to the production of pharmaceutical compositions, and such composition has pharmaceutically high quality, and may contain one or more agents selected from the group consisting of sweetener, flavor, colorant and preservative to provide a preparation having a good taste. A tablet contains an active ingredient mixed with a nontoxic excipient acceptable as a medicament, which is suitable for the production of tablet. Such excipient may be an inactive diluent such as calcium carbonate, sodium carbonate, lactose, calcium phosphate, sodium phosphate and the like, a granulating agent and a disintegrant such as cornstarch, alginic acid and the like, a binder such as starch, gelatin, acacia and the like, or a lubricant such as magnesium stearate, stearic acid, talc and the like. A tablet may not be coated or may be coated by a known technique for delaying disintegration and absorption in the gastrointestinal tract, whereby a sustained action is provided for a longer time. A composition for oral use may also be provided as a hard gelatin capsule containing an active ingredient mixed with inert solid diluent, such as calcium carbonate, calcium phosphate, kaolin, or as a soft gelatin capsule containing an active ingredient mixed with water or oil medium, such as peanut oil, liquid paraffin, olive oil. An aqueous suspension contains an active material mixed with an excipient suitable for the production of an aqueous suspension. An oily suspension can be prepared by suspending an active ingredient in an appropriate oil. An oil-in-water emulsion can also be adopted. Using a dispersible powder or granule suitable for the preparation of an aqueous suspension by adding water, an active ingredient mixed with a dispersing or wetting agent, a suspending agent, and one or more preservatives is provided. The pharmaceutical composition of the present invention may be in the form of a sterilized injectable aqueous or oily suspension. The medicament of the present invention can also be administered in the form of a suppository for rectal administration. For topical use, cream, ointment, jelly, solution, suspension and the like containing N-acetyl-D-mannosamine can be adopted. An N-acetyl-D-mannosamine preparation for administration by inhalation can also be provided. N-acetyl-D-mannosamine can also be administered by a transdermal patch according to a method known in the field.

EXAMPLES

The present invention is explained more specifically in the following by referring to Examples. The following shows representative Examples which are not limitative, and various applications are possible as long as they do not deviate from the technical idea of the present invention.

Example 1

Forced Swim Test (ManNAc Oral Administration)

<ManNac. Administration. Conditions>
ManNAc was dissolved in drinking water, and drinking water having a concentration of 5 mg/ml was administered to juvenile mice (C57BL/6 strain, male) by administration by free drinking of water for 4 weeks in total from 10-weekold to 14-week-old (ManNAc administration group: 16 mice). The mice of the control group in the same age in weeks were allowed to take drinking water freely (control group: 16 mice).

Similarly, 5 mg/ml ManNAc-containing drinking water was administered to aged mice (C57BL/6 strain, male) by administration by free drinking of water for 4 weeks in total from 56-week-old to 59-week-old (ManNAc administration group: 14 mice). The mice of the control group in the same age in weeks were allowed to take drinking water freely (control group: 15 mice).

<Forced Swim Test>

According to the method described in S. C. Dulawa et al., Neuropsychopharmacology (2004) 29, 1321-1330, water at 20-25° C. was filled in a plastic bucket (diameter about 28 cm, height about 18 cm) to a depth of about 12 cm, each mouse was left in the water tank solely for 6 min, and the behavior of the mouse was videotaped. The mice were graded with regard to 4 evaluation criteria: swimming, immobility, climbing, and others, and a dominant behavior was recorded every 5 sec. An experiment for 6 min per one time was repeated for 3 days. The results are shown in FIG. 1.

<Experiment Results>

When a mouse is forcibly placed in a water pool, it tries to swim to the shore. However, when a given time passes, it gives up and stops swimming (immobility). The forced swim test for 6 min enables quantification of immobility in a water tank, and the immobility has been proposed to be similar to "behavioral despair", observed in depression. A longer immobilization time shows a stronger depressive behavior, and a shorter immobilization time shows a weaker depressive behavior. As shown in FIG. 1, a total immobilization time of about 2 min was observed in the juvenile mouse control group, whereas a total immobilization time of about 1 min was observed in the ManNAc administration group. Therefrom it was acknowledged that ManNAc is superior in an antidepressant effect by oral administration, and has a remarkable depression improving effect.

As shown in FIG. 1, in the aged mouse control group, a total immobilization time of about 2 min 30 sec was observed, whereas a total immobilization time of about 1 min 40 sec-2min was observed in the ManNAc administration group. Therefrom it was acknowledged that ManNAc shows an improving effect by oral administration even for depressive symptoms in aged mouse.

<Discussion>

Figure 2:
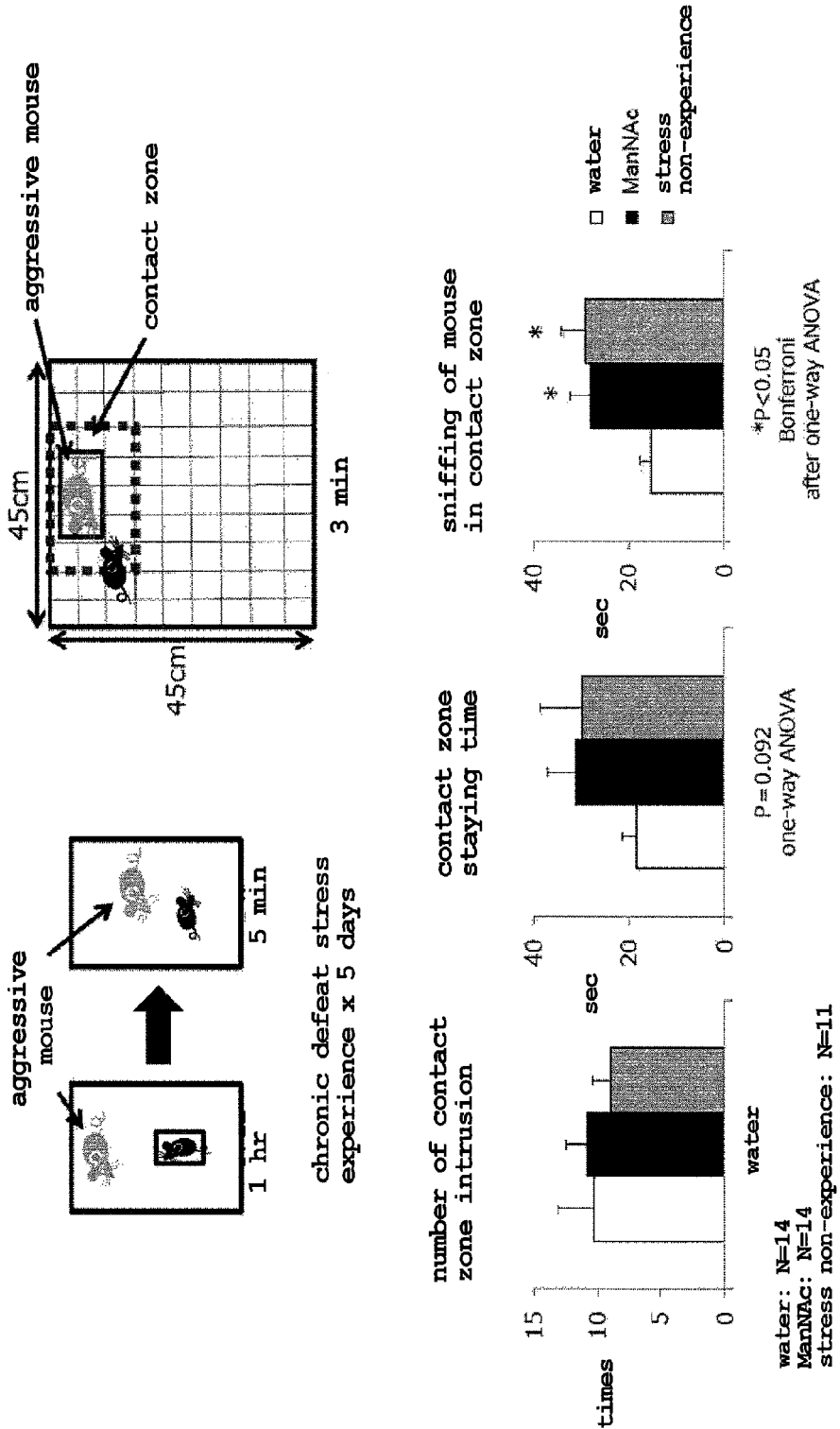
FIG. 2 shows an outline of the social defeat test of Example 2 and the results thereof.

In S. C. Dulawa et al., Neuropsychopharmacology (2004) 29, 1321-1330, a forced swim test similar to that in Example 1 of the present invention was performed to examine an antidepressant action of fluoxetine (SSRI) (page 1325, FIG. 2). As shown in FIG. 2, while the immobilization time varies depending on the strain of the mouse used, in BALB/c and C57BL/6 strains, about 125-130 sec (about 2 min) of immobilization time was observed in the drug non-administration group, whereas, in the fluoxetine (10 mg/kg/day) administration group, the immobilization time scarcely decreased as evidenced by about 100 sec for BALB/c strain and about 125 sec for C57BL/6 strain (page 1325, FIG. 2 b). While the weekly age of the mouse used in the forced swim test of S. C. Dulawa et al. is not clearly indicated, comparison with the results of the forced swim test using juvenile mouse in the present invention will be possible, in consideration of the immobilization time of the drug non-administration group. From the experiment results of the present invention, ManNAc is superior in the antidepressant effect, compared to the existing antidepressants.

Example 2

Social Defeat Test

<ManNac Administration Conditions>

Under conditions similar to those in Example 1, ManNAc was administered to juvenile mice (C57BL/6 strain, male) by administration by free drinking of water for 4 weeks in total from 10-week-old to 14-week-old (ManNAc administration group: 14 mice). The mice of the control group in the same age in weeks were allowed to take drinking water freely (control group: 14 mice).

<Social Defeat Test>

A mouse that lived with a more aggressive mouse (aggressive mouse) for a given period (1 hr) stays away from the aggressive mouse thereafter. This test method reflects higher brain functions, and was developed as a social defeat test and widely utilized as a system for evaluating social anxiety (Nature (2008) 455, 894-902). The ManNAc administration group and the control group were made to stay together with an aggressive mouse (one-to-one) for 1 hr per day, and the defeat stress was imposed for 5 days. Thereafter, the aggressive mouse housed in a particular compartment in a square compartment (45 cm one side) and the defeat stress experience mouse housed in the square compartment and allowed free mobility in the compartment other than the particular compartment were made to stay together for 5 min. The number of times the defeat stress experience mouse intruded a contact zone formed on the periphery of the compartment in which the aggressive mouse was housed, and the sniffing time of the defeat stress experience mouse were measured in the latter 3 minutes of 5 minutes. A mouse free of a defeat stress (stress non-experience group) was also tested similarly. The outline of the test and the results thereof are shown in FIG. 2.

<Experiment Results>

The mouse that experienced social defeat shows induction of a behavior to avoid society (aggressive mouse). Such avoidance behavior is similar to "Social Withdrawal" observed in depression. A less number of contact zone intrusion, and less contact zone staying time and sniffing time (peeping time) mean stronger depressive behavior, and higher levels of those mean weak depressive behavior. As shown in FIG. 2, while a significant difference was not found in the contact zone intrusion number, about 30 sec of sniffing behavior was observed in the stress non-experience group (drinking water administration, stress non-experience), but it decreased to about 20 sec or below in the defeat stress experience mouse (drinking water administration, water). In the ManNAc administration group, however, about 30 sec of sniffing behavior was observed, similar to the stress non-experience group. Therefrom it was found that ManNAc is also superior in an improving effect on the depression induced by social defeat experience.

Example 3

Forced Swim Test (5S-ManNAcF, ManNAc, Intracerebroventricular Administration)

<5S-ManNAcF, ManNAc Administration Conditions>

Using 8-9-week-old mice (C57BL/6 strain, male) having a catheter transplanted in the cerebroventricle, and carrying a connected osmotic pump (0.11 µl/hr, Alzet, No1004, 100 µl is released in 28 days) on the back, 5S-ManNAcF (0.01, 0.1 mmol/L) or ManNAc (100 mmol/L) dissolved in saline was intracerebroventricularly administered for 3 weeks (administration group: each 9-10 mice). The mice of the control group in the same age in weeks were administered with saline (control group: each 9-10 mice, SAL).

<Forced Swim Test>

Figure 3:
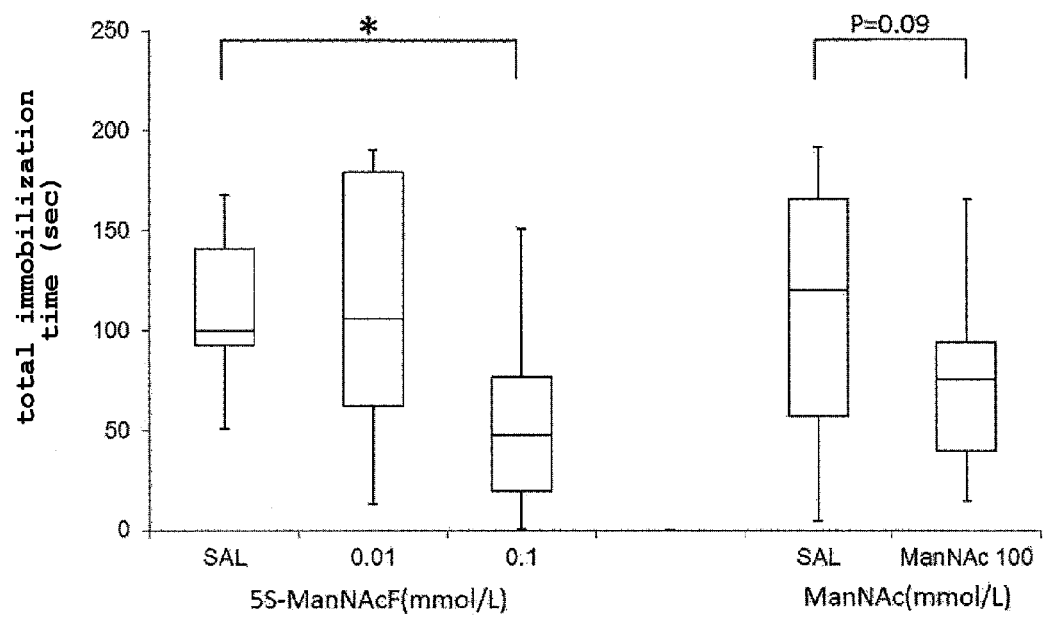
FIG. 3 shows the results of the forced swim test of Example 3, left Figure, *P<0.05: right Figure, P=0.09 (Welch's t-test)

A forced swim test similar to that in Example 1 was performed at 3 weeks after administration. The results are shown in FIG. 3.

<Experiment Results>

In the 0.1 mmol/L 5S-ManNAcF administration group, the total immobilization time significantly decreased as compared to the control group. Therefrom it was found that 5S-ManNAcF is superior in an antidepressant effect by intracerebroventricular administration, and has a remarkable depression improving effect.

Example 4

Forced Swim Test (5S-ManNAcF Intracerebroventricular Administration)

<5S-ManNAcF Administration Conditions>

Similar to Example 3, 5S-ManNAcF (0.01, 0.1, 1 mmol/L administration group: each 9-10 mice) was administered intracerebroventricularly. The dosing period was one week. The mice of the control group in the same age in weeks were administered with saline (control group: each 9-10 mice, SAL).

<Forced Swim Test>

Figure 4:
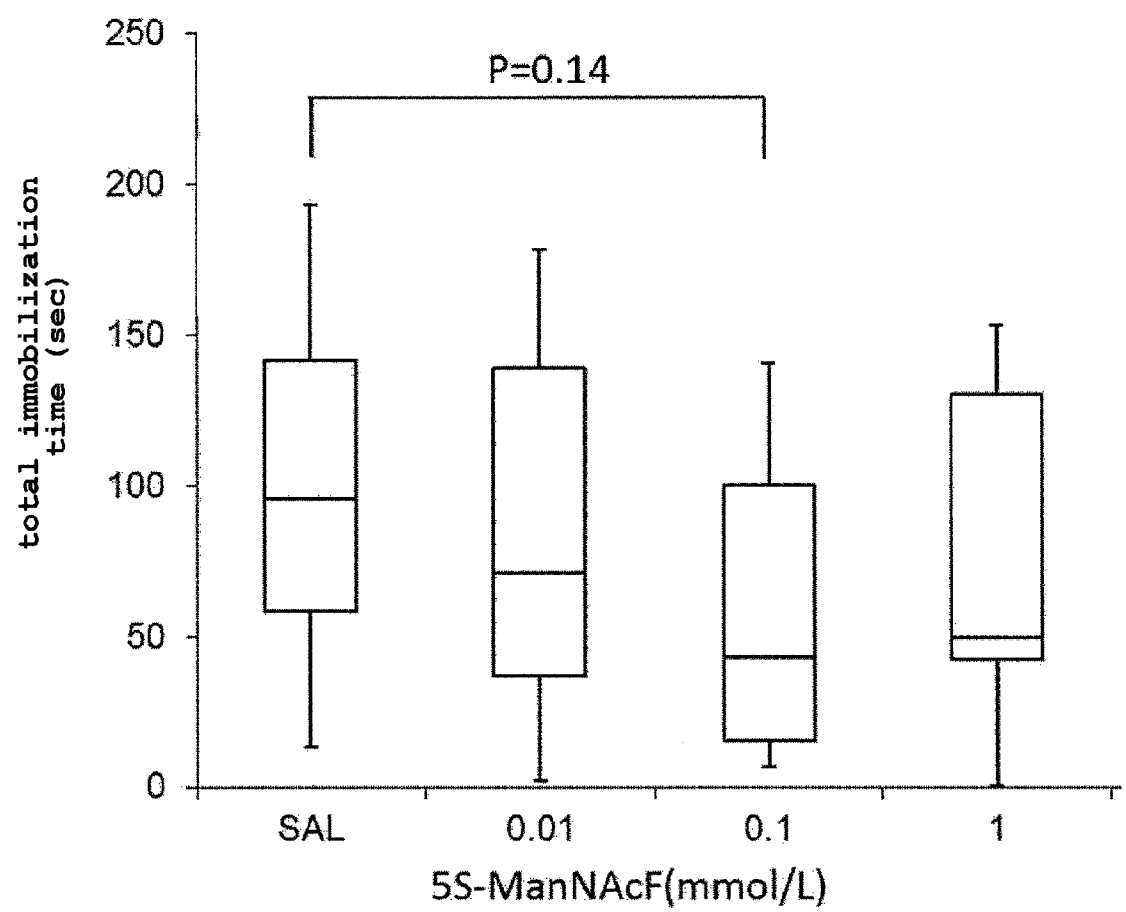
FIG. 4 shows the results of the forced swim test of Example 4. P=0.14 (Student's t-test)

A forced swim test similar to that in Example 1 was performed at 1 week after administration. The results are shown in FIG. 4.

<Experiment Results>

In the 0.1 mmol/L 5S-ManNAcF administration group, the total immobilization time significantly decreased as compared to the control group even by administration for one week. In addition, 5S-ManNAcF showed a tendency of a higher effect at a concentration of 0.1 mmol/L than a high dose of 1 mmol/L concentration.

INDUSTRIAL APPLICABILITY

The present invention provides a medicament, a food and the like containing N-acetyl-D-mannosamine as an active ingredient. Depression can be treated by medication or ingestion of the medicament or food of the present invention.

This application is based on a patent application No. 2014-102104 filed in Japan (filing date: May 16, 2014), the contents of which are incorporated in full herein.

The invention claimed is:

1. A method of treating depression, comprising a step of administering an effective amount of a N-acetyl-D-mannosamine compound to a subject in need thereof, wherein the N-acetyl-D-mannosamine compound is of formula (IIa), (IVa), (IVb), or (IVc):

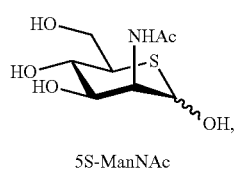

5S-ManNAc

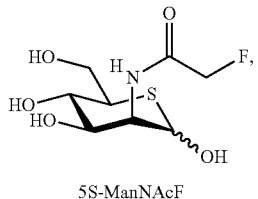

5S-ManNAcF

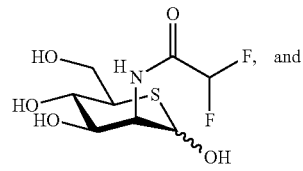

5S-ManNAcF$_2$

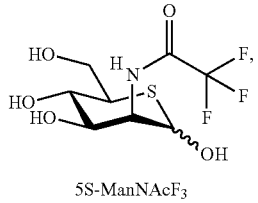

5S-ManNAcF$_3$ wherein Ac is an acetyl group,
or a salt thereof.

2. The treatment method according to claim 1, wherein the N-acetyl-D-mannosamine compound is of formula (IVa), (IVb), or (IVc):

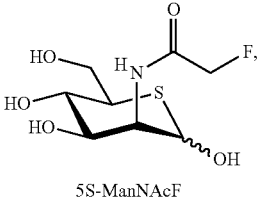

5S-ManNAcF

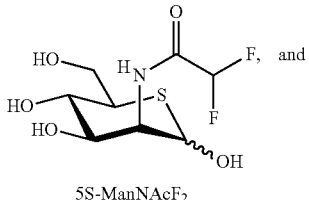

5S-ManNAcF$_2$

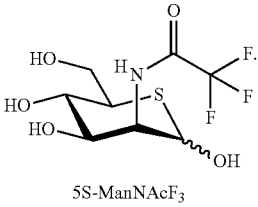

5S-ManNAcF$_3$

3. The treatment method according to claim 1, wherein the N-acetyl-D-mannosamine compound is of formula (IVa):

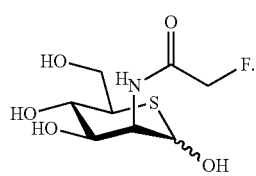

5S-ManNAcF (IVa)

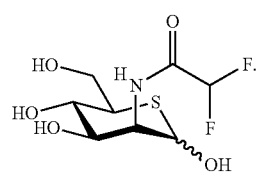

5S-ManNAcF$_2$ (IVb)

4. The treatment method according to claim 1, wherein the N-acetyl-D-mannosamine compound is of formula (IIa):

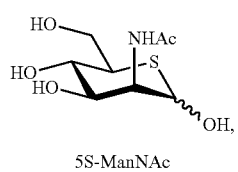

5S-ManNAc (IIa)

wherein Ac is an acetyl group.

5. The treatment method according to claim 1, wherein the N-acetyl-D-mannosamine compound is of formula (IVb):

6. The treatment method according to claim 1, wherein the N-acetyl-D-mannosamine compound is of formula (IVc):

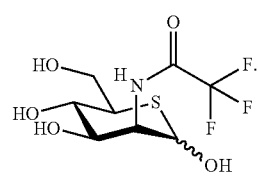

5S-ManNAcF$_3$ (IVc)

* * * * *